US012623049B2

(12) United States Patent
Snyder

(10) Patent No.: US 12,623,049 B2
(45) Date of Patent: May 12, 2026

(54) INTRAVASCULAR DEVICE WITH ENHANCED ONE-BEAM CUT PATTERN

(71) Applicant: Scientia Vascular, Inc., West Valley City, UT (US)

(72) Inventor: Edward J. Snyder, Park City, UT (US)

(73) Assignee: SCIENTIA VASCULAR, INC., West Valley City, UT (US)

( * ) Notice: Subject to any disclaimer, the term of this patent is extended or adjusted under 35 U.S.C. 154(b) by 0 days.

(21) Appl. No.: 16/855,366

(22) Filed: Apr. 22, 2020

(65) Prior Publication Data

US 2020/0345975 A1 Nov. 5, 2020

Related U.S. Application Data

(60) Provisional application No. 62/842,216, filed on May 2, 2019.

(51) Int. Cl.
| | |
|---|---|
| *A61M 25/00* | (2006.01) |
| *A61B 17/00* | (2006.01) |
| *A61M 25/09* | (2006.01) |

(52) U.S. Cl.
CPC ... *A61M 25/0015* (2013.01); *A61B 17/00234* (2013.01); *A61M 25/0054* (2013.01); *A61B 2017/00309* (2013.01); *A61M 2025/0042* (2013.01); *A61M 2025/09091* (2013.01); *A61M 2205/0266* (2013.01)

(58) Field of Classification Search
CPC .... A61B 17/00234; A61B 2017/00309; A61B 2017/00526; A61M 25/0054; A61M 2025/0042; A61M 2025/09091; A61M 2205/0266; A61M 25/0013; A61M 2025/09108; A61M 2025/09133; A61M 2025/09175; A61M 25/09; A61M 25/0051; A61M 25/0015; B26D 1/14; B26D 3/16
See application file for complete search history.

(56) References Cited

U.S. PATENT DOCUMENTS

| | | | |
|---|---|---|---|
| 2,022,065 A | 11/1935 | Wappler | |
| 2,187,299 A | 1/1940 | Burkhardt | |
(Continued)

FOREIGN PATENT DOCUMENTS

| | | |
|---|---|---|
| AU | 723040 | 12/1997 |
| AU | 733966 | 5/2001 |
(Continued)

OTHER PUBLICATIONS

Final Rejection received for U.S. Appl. No. 15/606,607, mailed on Dec. 15, 2020, 24 pages.
(Continued)

*Primary Examiner* — Richard G Louis
(74) *Attorney, Agent, or Firm* — Workman Nydegger

(57) ABSTRACT

Disclosed are intravascular devices having enhanced one-beam cut patterns. An elongated member includes a plurality of fenestrations that define a plurality of axially extending beams interspersed between a plurality of circumferentially extending rings. The beams are formed using a dual-pass cutting method in which a blade makes two, rotationally offset cutting passes at a given longitudinal location of the elongated member. The resulting beam has enhanced structure that avoids overly sharp edges and minimizes structural weak points.

18 Claims, 5 Drawing Sheets

(56)               References Cited

U.S. PATENT DOCUMENTS

| | | | |
|---|---|---|---|
| 3,183,702 A | | 5/1965 | Zittel |
| 3,431,650 A | * | 3/1969 | De Mattia ............. G01C 21/02 |
| | | | 33/431 |
| 3,572,334 A | | 3/1971 | Petterson |
| 3,612,058 A | | 10/1971 | Ackerman |
| 3,709,271 A | | 1/1973 | Flory |
| 3,782,233 A | | 1/1974 | Helm |
| 3,920,058 A | | 11/1975 | Walker |
| 4,163,406 A | | 8/1979 | Crawford |
| 4,239,069 A | | 12/1980 | Zimmerman |
| 4,416,312 A | | 11/1983 | Ostberg |
| 4,688,540 A | | 8/1987 | Ono |
| 4,719,924 A | | 1/1988 | Crittenden |
| 4,801,297 A | | 1/1989 | Mueller |
| 4,846,186 A | | 7/1989 | Box |
| 4,895,168 A | | 1/1990 | Machek |
| 4,989,608 A | | 2/1991 | Ratner |
| 5,047,045 A | | 9/1991 | Arney et al. |
| 5,069,217 A | | 12/1991 | Fleischhacker |
| 5,084,022 A | | 1/1992 | Claude |
| 5,095,915 A | | 3/1992 | Angelson |
| 5,102,390 A | | 4/1992 | Crittenden et al. |
| 5,144,959 A | | 9/1992 | Gambale et al. |
| 5,147,317 A | | 9/1992 | Shank |
| 5,154,725 A | | 10/1992 | Leopold |
| 5,174,302 A | | 12/1992 | Palmer |
| 5,315,996 A | | 5/1994 | Lundquist |
| 5,326,374 A | | 7/1994 | Ilbawi et al. |
| 5,345,945 A | | 9/1994 | Hodgson et al. |
| 5,366,464 A | | 11/1994 | Belknap |
| 5,372,587 A | | 12/1994 | Hammerslag |
| 5,381,782 A | | 1/1995 | Delarama et al. |
| 5,382,259 A | | 1/1995 | Phelps |
| 5,385,152 A | | 1/1995 | Abele |
| 5,437,288 A | | 8/1995 | Schwartz |
| 5,441,483 A | | 8/1995 | Avitall |
| D363,544 S | | 10/1995 | Rowland et al. |
| D363,776 S | | 10/1995 | Rowland et al. |
| 5,480,382 A | | 1/1996 | Hammerslag et al. |
| 5,506,682 A | | 4/1996 | Pryor |
| 5,507,751 A | | 4/1996 | Goode et al. |
| 5,551,444 A | | 9/1996 | Finlayson |
| 5,554,114 A | | 9/1996 | Wallace et al. |
| 5,569,218 A | | 10/1996 | Berg |
| 5,573,520 A | | 11/1996 | Schwartz |
| 5,573,867 A | | 11/1996 | Zafred et al. |
| 5,606,981 A | | 3/1997 | Tartacower et al. |
| 5,659,205 A | | 8/1997 | Weisser |
| 5,673,707 A | | 10/1997 | Chandrasekaran |
| 5,676,659 A | | 10/1997 | McGurk |
| 5,685,568 A | | 11/1997 | Pirrello |
| 5,685,868 A | | 11/1997 | Lundquist |
| 5,690,120 A | | 11/1997 | Jacobsen |
| 5,706,826 A | | 1/1998 | Schwager |
| 5,741,429 A | | 4/1998 | Donadio |
| 5,746,701 A | | 5/1998 | Noone |
| 5,792,154 A | | 8/1998 | Doan |
| 5,797,857 A | | 8/1998 | Obitsu |
| 5,800,454 A | | 9/1998 | Jacobsen |
| 5,833,631 A | | 11/1998 | Nguyen |
| 5,833,632 A | | 11/1998 | Jacobsen |
| 5,842,461 A | | 12/1998 | Azuma |
| 5,860,963 A | | 1/1999 | Azam |
| 5,876,356 A | | 3/1999 | Viera et al. |
| 5,911,715 A | | 6/1999 | Berg |
| 5,911,717 A | | 6/1999 | Jacobsen |
| 5,916,194 A | | 6/1999 | Jacobsen |
| 5,931,830 A | | 8/1999 | Jacobsen |
| 5,954,672 A | | 9/1999 | Schwager |
| 6,004,279 A | | 12/1999 | Crowley |
| 6,014,919 A | | 1/2000 | Jacobsen |
| 6,017,319 A | | 1/2000 | Jacobsen |
| 6,022,343 A | | 2/2000 | Johnson et al. |
| 6,022,369 A | | 2/2000 | Jacobsen |
| 6,027,526 A | | 2/2000 | Limon et al. |
| 6,027,863 A | | 2/2000 | Donadis |
| 6,033,288 A | | 3/2000 | Weisshaus |
| 6,033,394 A | | 3/2000 | Vidlund |
| 6,056,702 A | | 5/2000 | Lorenzo |
| 6,063,101 A | | 5/2000 | Jacobsen |
| 6,110,164 A | | 8/2000 | Vidlund |
| 6,132,389 A | | 10/2000 | Cornish |
| 6,139,511 A | | 10/2000 | Huter |
| D435,909 S | | 1/2001 | Ogino et al. |
| 6,168,570 B1 | | 1/2001 | Ferrera |
| 6,179,828 B1 | | 1/2001 | Mottola |
| 6,183,410 B1 | | 2/2001 | Jacobsen |
| 6,183,420 B1 | | 2/2001 | Douk et al. |
| 6,214,042 B1 | | 4/2001 | Jacobsen |
| 6,228,073 B1 | | 5/2001 | Noone |
| 6,245,030 B1 | | 6/2001 | Dubois |
| 6,251,086 B1 | | 6/2001 | Cornelius |
| 6,260,458 B1 | | 7/2001 | Jacobsen |
| 6,261,246 B1 | | 7/2001 | Pantages |
| 6,273,881 B1 | | 8/2001 | Kiemeneij |
| 6,302,870 B1 | | 10/2001 | Jacobsen |
| 6,306,105 B1 | | 10/2001 | Rooney |
| 6,346,091 B1 | | 2/2002 | Jacobsen |
| 6,356,791 B1 | | 3/2002 | Westlund |
| 6,402,706 B2 | | 6/2002 | Richardson et al. |
| 6,428,489 B1 | | 8/2002 | Jacobsen |
| 6,431,039 B1 | | 8/2002 | Jacobsen |
| 6,436,056 B1 | | 8/2002 | Wang et al. |
| 6,440,088 B1 | | 8/2002 | Jacobsen |
| 6,458,867 B1 | | 10/2002 | Wang et al. |
| 6,464,651 B1 | | 10/2002 | Hiejima et al. |
| 6,492,615 B1 | | 12/2002 | Flanagan |
| 6,494,894 B2 | | 12/2002 | Mirarchi |
| 6,527,732 B1 | | 3/2003 | Strauss |
| 6,527,746 B1 | | 3/2003 | Oslund |
| 6,553,880 B2 | | 4/2003 | Jacobsen |
| 6,554,820 B1 | | 4/2003 | Wendlandt |
| 6,558,355 B1 | | 5/2003 | Metzger |
| 6,579,246 B2 | | 6/2003 | Jacobsen |
| 6,602,207 B1 | | 8/2003 | Mam |
| 6,606,985 B2 | | 8/2003 | Negishi |
| 6,610,046 B1 | | 8/2003 | Usami et al. |
| 6,627,724 B2 | | 9/2003 | Meijs et al. |
| 6,652,508 B2 | | 11/2003 | Griffin |
| 6,671,560 B2 | | 12/2003 | Westlund |
| 6,766,720 B1 | | 7/2004 | Jacobsen |
| 6,805,676 B2 | | 10/2004 | Klint |
| 6,866,642 B2 | | 3/2005 | Kellerman et al. |
| RE39,018 E | | 3/2006 | Azuma |
| 7,024,885 B2 | | 4/2006 | Rold |
| 7,097,624 B2 | | 8/2006 | Campion |
| 7,110,910 B1 | | 9/2006 | Deffenbaugh |
| 7,128,718 B2 | | 10/2006 | Hojeibane et al. |
| 7,172,587 B2 | | 2/2007 | Poole et al. |
| 7,182,735 B2 | | 2/2007 | Shireman |
| 7,276,062 B2 | | 10/2007 | McDaniel et al. |
| 7,338,345 B2 | | 3/2008 | Fujinami |
| 7,421,929 B2 | | 9/2008 | French |
| 7,494,474 B2 | | 2/2009 | Richardson et al. |
| 7,507,246 B2 | | 3/2009 | McGuckin et al. |
| D598,094 S | | 8/2009 | Alber |
| 7,621,880 B2 | | 11/2009 | Ryan |
| 7,637,875 B2 | | 12/2009 | Itou |
| 7,641,622 B2 | | 1/2010 | Satou |
| D611,596 S | | 3/2010 | Kousai et al. |
| 7,670,302 B2 | | 3/2010 | Griffin |
| 7,699,792 B2 | | 4/2010 | Hofmann |
| 7,722,545 B2 | | 5/2010 | Bertsch |
| 7,722,552 B2 | | 5/2010 | Aimi |
| 7,744,545 B2 | | 6/2010 | Aimi |
| 7,747,314 B2 | | 6/2010 | Parins |
| 7,753,859 B2 | | 7/2010 | Kinoshita |
| 7,766,896 B2 | | 8/2010 | Volk |
| 7,769,839 B2 | | 8/2010 | Boivie et al. |
| 7,785,273 B2 | | 8/2010 | Eskuri |
| 7,789,839 B2 | | 9/2010 | Lupton |
| 7,806,837 B2 | | 10/2010 | Rasmussen |
| 7,878,984 B2 | | 2/2011 | Davis |
| 7,883,474 B1 | | 2/2011 | Mirigian |

(56)                  References Cited

U.S. PATENT DOCUMENTS

| | | | |
|---|---|---|---|
| 7,914,467 B2 | 3/2011 | Layman et al. | |
| 7,942,832 B2 | 5/2011 | Kanuka | |
| 7,967,762 B2 | 6/2011 | Corl et al. | |
| 7,989,042 B2 | 8/2011 | Obara et al. | |
| 8,007,434 B2 | 8/2011 | Olson | |
| 8,043,314 B2 | 10/2011 | Noriega et al. | |
| 8,048,004 B2 | 11/2011 | Davis et al. | |
| 8,092,444 B2 | 1/2012 | Lentz et al. | |
| 8,105,246 B2 | 1/2012 | Voeller | |
| 8,128,579 B2 | 3/2012 | Chen | |
| 8,128,580 B2 | 3/2012 | Fujimagari | |
| 8,137,293 B2 | 3/2012 | Zhou | |
| 8,167,821 B2 | 5/2012 | Sharrow et al. | |
| 8,257,279 B2 | 9/2012 | Jacobsen | |
| 8,292,827 B2 | 10/2012 | Musbach et al. | |
| 8,292,828 B2 | 10/2012 | Uihlein | |
| 8,357,140 B2 | 1/2013 | Majercak | |
| 8,376,865 B2 | 2/2013 | Forster et al. | |
| 8,376,961 B2 | 2/2013 | Layman | |
| 8,377,056 B2 | 2/2013 | Oyola et al. | |
| 8,409,114 B2 | 4/2013 | Parins | |
| 8,409,169 B1 * | 4/2013 | Moss | A61M 25/0012 |
| | | | 604/524 |
| 8,444,577 B2 | 5/2013 | Bunch | |
| 8,454,535 B2 | 6/2013 | Majercak | |
| 8,460,213 B2 | 6/2013 | Northrop | |
| 8,465,469 B2 | 6/2013 | Brightbill | |
| 8,468,919 B2 | 6/2013 | Christian | |
| 8,500,658 B2 | 8/2013 | Boyle | |
| 8,517,959 B2 | 8/2013 | Kurosawa | |
| 8,535,243 B2 | 9/2013 | Shireman | |
| 8,540,648 B2 | 9/2013 | Uihlein | |
| 8,540,668 B2 | 9/2013 | Griffin et al. | |
| 8,551,020 B2 | 10/2013 | Chen et al. | |
| 8,551,021 B2 | 10/2013 | Voeller | |
| 8,556,914 B2 | 10/2013 | Vrba | |
| 8,585,643 B2 | 11/2013 | Vo et al. | |
| 8,622,931 B2 | 1/2014 | Teague | |
| 8,622,933 B2 | 1/2014 | Maki | |
| 8,636,270 B2 | 1/2014 | Ostrovsky | |
| 8,728,075 B2 | 5/2014 | Wu et al. | |
| 8,758,269 B2 | 6/2014 | Miyata et al. | |
| 8,784,337 B2 | 7/2014 | Voeller et al. | |
| 8,795,202 B2 | 8/2014 | Northrop | |
| 8,795,254 B2 | 8/2014 | Layman | |
| 8,821,477 B2 | 9/2014 | Northrop | |
| 8,870,790 B2 | 10/2014 | Jacobsen | |
| 8,900,163 B2 | 12/2014 | Jacobsen | |
| 8,915,865 B2 | 12/2014 | Jacobsen et al. | |
| 8,932,235 B2 | 1/2015 | Jacobsen | |
| 8,936,558 B2 | 1/2015 | Jacobsen | |
| 8,939,916 B2 | 1/2015 | Jacobsen | |
| 8,956,310 B2 | 2/2015 | Miyata | |
| 9,011,511 B2 | 4/2015 | Gregorich et al. | |
| 9,067,332 B2 | 6/2015 | Lippert | |
| 9,067,333 B2 | 6/2015 | Lippert | |
| 9,072,873 B2 | 7/2015 | Lippert | |
| 9,072,874 B2 | 7/2015 | Northrop | |
| D742,000 S | 10/2015 | Kanazawa | |
| 9,162,040 B2 | 10/2015 | Vo et al. | |
| 9,227,037 B2 | 1/2016 | Northrop | |
| 9,254,143 B2 | 2/2016 | Huynh et al. | |
| 9,364,589 B2 | 6/2016 | Cage | |
| 9,375,234 B2 | 6/2016 | Vrba | |
| 9,433,762 B2 | 9/2016 | Griffin et al. | |
| 9,439,557 B2 | 9/2016 | Boulais | |
| 9,550,013 B2 | 1/2017 | Kawasaki | |
| 9,616,195 B2 | 4/2017 | Lippert | |
| 9,623,212 B2 | 4/2017 | Tano | |
| 9,662,798 B2 | 5/2017 | Christian | |
| 9,700,702 B2 | 7/2017 | Tano | |
| 9,808,595 B2 | 11/2017 | Turnlund et al. | |
| 9,839,764 B2 | 12/2017 | Chouinard | |
| 9,848,882 B2 | 12/2017 | Lippert | |
| D809,138 S | 1/2018 | Khan et al. | |
| 9,950,137 B2 | 4/2018 | Lippert | |
| 9,999,748 B2 | 6/2018 | Cajamarca et al. | |
| 10,016,210 B2 | 7/2018 | Lenker et al. | |
| 10,028,666 B2 | 7/2018 | Gregorich | |
| 10,052,013 B2 | 8/2018 | Boulais | |
| 10,149,608 B2 | 12/2018 | Fujitani | |
| D839,426 S | 1/2019 | Bajwa | |
| D847,335 S | 4/2019 | Kuwada | |
| 10,252,024 B2 | 4/2019 | Northrop | |
| D855,180 S | 7/2019 | Haefliger | |
| 10,350,383 B2 | 7/2019 | Shuman | |
| 10,363,389 B2 | 7/2019 | Lippert | |
| D855,800 S | 8/2019 | Gabay et al. | |
| 10,420,537 B2 | 9/2019 | Salahieh et al. | |
| 10,441,746 B2 | 10/2019 | Besselink | |
| 10,456,556 B2 | 10/2019 | Cabiri | |
| 10,639,456 B2 | 5/2020 | Peralta | |
| 10,675,057 B2 | 6/2020 | Krieger et al. | |
| 10,675,444 B2 | 6/2020 | Kauphusman et al. | |
| 10,758,710 B2 | 9/2020 | Romano | |
| 10,806,893 B2 | 10/2020 | Jaroch | |
| 10,821,268 B2 | 11/2020 | Snyder et al. | |
| 10,835,183 B2 | 11/2020 | Sham et al. | |
| 11,007,345 B2 | 5/2021 | Cottone | |
| 11,052,226 B2 | 7/2021 | Salahieh et al. | |
| 11,141,566 B2 | 10/2021 | Cabiri | |
| D946,148 S | 3/2022 | Takemoto | |
| 11,278,704 B2 | 3/2022 | Pleijers | |
| 11,305,095 B2 | 4/2022 | Snyder et al. | |
| 11,317,938 B2 | 5/2022 | Lenker et al. | |
| 11,369,351 B2 | 6/2022 | Davis et al. | |
| 11,383,068 B2 | 7/2022 | Tran et al. | |
| 11,471,645 B2 | 10/2022 | Mcniven et al. | |
| 11,497,512 B2 | 11/2022 | Wallace et al. | |
| 11,565,093 B2 | 1/2023 | Kirt et al. | |
| D980,427 S | 3/2023 | Method et al. | |
| 11,679,236 B2 | 6/2023 | Von et al. | |
| 11,724,065 B2 | 8/2023 | Tilson et al. | |
| 11,724,068 B2 | 8/2023 | Von et al. | |
| 11,759,217 B2 | 9/2023 | Keating et al. | |
| 11,766,539 B2 | 9/2023 | Yee et al. | |
| D1,014,751 S | 2/2024 | Shih | |
| 11,896,757 B2 | 2/2024 | Tran et al. | |
| 11,918,753 B2 | 3/2024 | Moquin et al. | |
| 11,957,312 B2 | 4/2024 | Boulais | |
| 2001/0009980 A1 | 7/2001 | Richardson et al. | |
| 2001/0044624 A1 | 11/2001 | Seraj et al. | |
| 2002/0013540 A1 | 1/2002 | Jacobsen et al. | |
| 2002/0019599 A1 | 2/2002 | Rooney | |
| 2002/0049392 A1 | 4/2002 | DeMello | |
| 2002/0062524 A1 | 5/2002 | Vogland et al. | |
| 2002/0068912 A1 | 6/2002 | Merdan | |
| 2002/0078808 A1 | 6/2002 | Jacobsen et al. | |
| 2002/0082524 A1 | 6/2002 | Anderson | |
| 2003/0009208 A1 | 1/2003 | Snyder et al. | |
| 2003/0023190 A1 | 1/2003 | Cox | |
| 2003/0060732 A1 | 3/2003 | Jacobsen et al. | |
| 2003/0069521 A1 | 4/2003 | Reynolds et al. | |
| 2003/0069522 A1 | 4/2003 | Jacobsen | |
| 2003/0093059 A1 | 5/2003 | Griffin et al. | |
| 2003/0125641 A1 | 7/2003 | Jafari et al. | |
| 2004/0039371 A1 | 2/2004 | Tockman et al. | |
| 2004/0054349 A1 | 3/2004 | Brightbill | |
| 2004/0087933 A1 | 5/2004 | Lee | |
| 2004/0093060 A1 | 5/2004 | Seguin et al. | |
| 2004/0102719 A1 | 5/2004 | Keith et al. | |
| 2004/0102720 A1 | 5/2004 | Kellerman et al. | |
| 2004/0111044 A1 * | 6/2004 | Davis | A61M 25/09016 |
| | | | 600/585 |
| 2004/0122340 A1 | 6/2004 | Vrba et al. | |
| 2004/0167437 A1 | 8/2004 | Sharrow et al. | |
| 2004/0167440 A1 | 8/2004 | Sharrow et al. | |
| 2004/0167443 A1 | 8/2004 | Shireman et al. | |
| 2004/0171996 A1 | 9/2004 | Kiemeneij | |
| 2004/0181174 A2 * | 9/2004 | Davis | A61M 25/01 |
| | | | 600/585 |
| 2004/0186485 A1 | 9/2004 | Kear | |
| 2004/0193140 A1 | 9/2004 | Griffin | |
| 2004/0225292 A1 | 11/2004 | Sasso et al. | |

(56)                References Cited

U.S. PATENT DOCUMENTS

| | | |
|---|---|---|
| 2004/0254450 A1 | 12/2004 | Griffin et al. |
| 2005/0054953 A1 | 3/2005 | Ryan |
| 2005/0065456 A1 | 3/2005 | Eskuri |
| 2005/0124976 A1 | 6/2005 | Devens, Jr. et al. |
| 2005/0137501 A1 | 6/2005 | Euteneuer et al. |
| 2005/0216049 A1 | 9/2005 | Jones et al. |
| 2005/0274384 A1 | 12/2005 | Tran et al. |
| 2006/0006649 A1 | 1/2006 | Galdonik et al. |
| 2006/0041186 A1 | 2/2006 | Vancaillie |
| 2006/0074442 A1 | 4/2006 | Noriega |
| 2006/0089618 A1 | 4/2006 | McFerran |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0241519 A1 | 10/2006 | Hojeibane et al. |
| 2006/0262474 A1 | 11/2006 | Chen et al. |
| 2007/0010786 A1 | 1/2007 | Casey et al. |
| 2007/0055302 A1 | 3/2007 | Henry et al. |
| 2007/0100285 A1 | 5/2007 | Griffin |
| 2007/0112331 A1 | 5/2007 | Weber et al. |
| 2007/0135763 A1 | 6/2007 | Musbach |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0208405 A1 | 9/2007 | Goodin et al. |
| 2007/0213689 A1 | 9/2007 | Grewe et al. |
| 2007/0221230 A1 | 9/2007 | Thompson |
| 2007/0233039 A1 | 10/2007 | Mitelberg |
| 2007/0250036 A1 | 10/2007 | Volk |
| 2007/0282270 A1 | 12/2007 | Mathews et al. |
| 2007/0287955 A1 | 12/2007 | Layman et al. |
| 2008/0021347 A1 | 1/2008 | Jacobsen et al. |
| 2008/0021401 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021406 A1 | 1/2008 | Jacobsen et al. |
| 2008/0033421 A1 | 2/2008 | Davis et al. |
| 2008/0064989 A1 | 3/2008 | Chen et al. |
| 2008/0077049 A1 | 3/2008 | Hirshman |
| 2008/0086854 A1 | 4/2008 | Boyd |
| 2008/0097246 A1 | 4/2008 | Stafford |
| 2008/0097247 A1 | 4/2008 | Eskuri |
| 2008/0097248 A1 | 4/2008 | Munoz |
| 2008/0114303 A1* | 5/2008 | Tremaglio ............ A61M 25/09 604/164.13 |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0140101 A1 | 6/2008 | Carley et al. |
| 2008/0147170 A1 | 6/2008 | Vrba |
| 2008/0188298 A1 | 8/2008 | Seelig et al. |
| 2008/0188928 A1 | 8/2008 | Salahieh |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu |
| 2009/0036832 A1 | 2/2009 | Skujins et al. |
| 2009/0036833 A1 | 2/2009 | Parins |
| 2009/0043283 A1 | 2/2009 | Turnlund et al. |
| 2009/0043372 A1 | 2/2009 | Northrop et al. |
| 2009/0043483 A1 | 2/2009 | Abe et al. |
| 2009/0118675 A1 | 5/2009 | Czyscon et al. |
| 2009/0118704 A1 | 5/2009 | Sharrow et al. |
| 2009/0163945 A1 | 6/2009 | Richard et al. |
| 2009/0177119 A1 | 7/2009 | Heidner |
| 2009/0177185 A1* | 7/2009 | Northrop ............. A61B 1/0011 604/528 |
| 2009/0254000 A1 | 10/2009 | Layman et al. |
| 2009/0292225 A1 | 11/2009 | Chen et al. |
| 2009/0318892 A1 | 12/2009 | Aboytes et al. |
| 2010/0030186 A1 | 2/2010 | Stivland |
| 2010/0063479 A1 | 3/2010 | Merddan |
| 2010/0069882 A1 | 3/2010 | Jennings et al. |
| 2010/0114017 A1 | 5/2010 | Lenker et al. |
| 2010/0114302 A1 | 5/2010 | Tzafriri et al. |
| 2010/0139465 A1 | 6/2010 | Christian et al. |
| 2010/0145308 A1 | 6/2010 | Layman et al. |
| 2010/0228150 A1 | 9/2010 | Zimmerman |
| 2010/0256527 A1 | 10/2010 | Lippert et al. |
| 2010/0256528 A1* | 10/2010 | Lippert ................. A61M 25/09 600/585 |
| 2010/0256601 A1 | 10/2010 | Lippert et al. |
| 2010/0256602 A1 | 10/2010 | Lippert et al. |
| 2010/0256603 A1 | 10/2010 | Lippert |
| 2010/0256604 A1 | 10/2010 | Lippert |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa |
| 2011/0022003 A1 | 1/2011 | Tekulve |
| 2011/0160680 A1 | 6/2011 | Cage et al. |
| 2011/0245807 A1* | 10/2011 | Sakata ................ A61M 25/005 604/526 |
| 2011/0245808 A1 | 10/2011 | Voeller et al. |
| 2011/0251519 A1 | 10/2011 | Romoscanu |
| 2011/0313417 A1 | 12/2011 | De et al. |
| 2012/0046575 A1 | 2/2012 | Brown |
| 2012/0065623 A1 | 3/2012 | Nelson, III |
| 2012/0158034 A1 | 6/2012 | Wilson |
| 2012/0209073 A1 | 8/2012 | McWeeney et al. |
| 2012/0239074 A1 | 9/2012 | Aboytes et al. |
| 2012/0271397 A1 | 10/2012 | Muzslay et al. |
| 2012/0289938 A1 | 11/2012 | Northrop et al. |
| 2013/0018280 A1 | 1/2013 | Tano et al. |
| 2013/0018359 A1 | 1/2013 | Coyle |
| 2013/0096553 A1 | 4/2013 | Hill et al. |
| 2013/0110000 A1 | 5/2013 | Tully |
| 2013/0131642 A1 | 5/2013 | Miyata et al. |
| 2013/0144267 A1 | 6/2013 | Chan et al. |
| 2013/0184703 A1 | 7/2013 | Shireman et al. |
| 2013/0226033 A1 | 8/2013 | Eskuri |
| 2013/0255456 A1 | 10/2013 | Christian |
| 2013/0274784 A1 | 10/2013 | Lenker et al. |
| 2014/0012281 A1 | 1/2014 | Wang et al. |
| 2014/0031719 A1 | 1/2014 | Kanazawa |
| 2014/0058324 A1 | 2/2014 | Salahieh et al. |
| 2014/0094787 A1 | 4/2014 | Reynolds |
| 2014/0187983 A1 | 7/2014 | Anderson |
| 2014/0257363 A1 | 9/2014 | Lippert |
| 2014/0276109 A1 | 9/2014 | Gregorich |
| 2014/0276117 A1 | 9/2014 | Burkett |
| 2014/0276787 A1 | 9/2014 | Wang et al. |
| 2014/0279109 A1 | 9/2014 | Vasquez et al. |
| 2014/0309657 A1 | 10/2014 | Ben-Ami |
| 2014/0336620 A1 | 11/2014 | Layman et al. |
| 2014/0343538 A1 | 11/2014 | Lenker et al. |
| 2015/0011834 A1 | 1/2015 | Ayala et al. |
| 2015/0011964 A1 | 1/2015 | Abner |
| 2015/0057639 A1 | 2/2015 | Storbeck et al. |
| 2015/0190614 A1 | 7/2015 | Uihlein |
| 2015/0190615 A1 | 7/2015 | Shaltis |
| 2015/0216533 A1* | 8/2015 | Gray ................ A61B 17/12109 606/195 |
| 2015/0238734 A1 | 8/2015 | Kanazawa |
| 2015/0290432 A1 | 10/2015 | Matthews |
| 2015/0297863 A1 | 10/2015 | Hannon et al. |
| 2015/0305710 A1 | 10/2015 | Koninklijke |
| 2015/0306355 A1 | 10/2015 | Idstrom |
| 2016/0001048 A1 | 1/2016 | Koike |
| 2016/0008585 A1 | 1/2016 | Tano |
| 2016/0045101 A1 | 2/2016 | Nakatate et al. |
| 2016/0058382 A1 | 3/2016 | Burkett et al. |
| 2016/0089128 A1 | 3/2016 | Weber et al. |
| 2016/0113793 A1 | 4/2016 | Nishigishi |
| 2016/0135827 A1 | 5/2016 | Elsesser |
| 2016/0199620 A1 | 7/2016 | Pokorney |
| 2016/0235337 A1 | 8/2016 | Govari |
| 2016/0287054 A1 | 10/2016 | Fujitani |
| 2016/0310702 A1 | 10/2016 | Cabiri |
| 2016/0361520 A1 | 12/2016 | Braun |
| 2016/0367788 A1 | 12/2016 | Jimenez et al. |
| 2016/0375226 A1 | 12/2016 | Nabeshima |
| 2017/0047740 A1 | 2/2017 | Narla |
| 2017/0049594 A1 | 2/2017 | Banas et al. |

(56) References Cited

U.S. PATENT DOCUMENTS

| | | | |
|---|---|---|---|
| 2017/0136213 A1 | 5/2017 | Kauphusman et al. | |
| 2017/0189643 A1 | 7/2017 | Christian | |
| 2017/0203076 A1 | 7/2017 | Groneberg et al. | |
| 2017/0215954 A1 | 8/2017 | Datta et al. | |
| 2017/0234411 A1 | 8/2017 | Dewaele et al. | |
| 2017/0281909 A1 | 10/2017 | Northrop et al. | |
| 2018/0015260 A1 | 1/2018 | Sano et al. | |
| 2018/0015261 A1 | 1/2018 | Lippert | |
| 2018/0015262 A1 | 1/2018 | Lippert | |
| 2018/0015263 A1 | 1/2018 | Lippert | |
| 2018/0028177 A1 | 2/2018 | Van et al. | |
| 2018/0071496 A1* | 3/2018 | Snyder ............... | A61M 25/0052 |
| 2018/0177517 A1 | 6/2018 | Lippert | |
| 2018/0185619 A1 | 7/2018 | Batman et al. | |
| 2018/0193603 A1 | 7/2018 | Falb et al. | |
| 2018/0193607 A1 | 7/2018 | Lippert | |
| 2018/0207407 A1 | 7/2018 | Tanigaki | |
| 2019/0008639 A1 | 1/2019 | Landon et al. | |
| 2019/0105463 A1 | 4/2019 | Christian et al. | |
| 2019/0175869 A1 | 6/2019 | Kirt et al. | |
| 2019/0255290 A1 | 8/2019 | Snyder et al. | |
| 2019/0290883 A1 | 9/2019 | Lippert et al. | |
| 2019/0358434 A1 | 11/2019 | Fuller et al. | |
| 2020/0016378 A1 | 1/2020 | Williams et al. | |
| 2020/0054860 A1* | 2/2020 | McElhaney ........ | G05B 19/4155 |
| 2020/0094027 A1 | 3/2020 | Davis | |
| 2020/0121308 A1 | 4/2020 | Davis et al. | |
| 2020/0222666 A1 | 7/2020 | Chan et al. | |
| 2020/0222672 A1 | 7/2020 | Davis et al. | |
| 2020/0330734 A1 | 10/2020 | Sugita et al. | |
| 2021/0008351 A1 | 1/2021 | Snyder et al. | |
| 2021/0022748 A1 | 1/2021 | Lorenzo | |
| 2021/0162184 A1 | 6/2021 | Lippert et al. | |
| 2021/0178128 A1 | 6/2021 | Lippert et al. | |
| 2021/0213241 A1 | 7/2021 | Christian et al. | |
| 2021/0228845 A1 | 7/2021 | Lippert et al. | |
| 2021/0283372 A1 | 9/2021 | Murphy | |
| 2021/0283380 A1 | 9/2021 | Lippert et al. | |
| 2021/0307766 A1 | 10/2021 | Keating et al. | |
| 2021/0346656 A1 | 11/2021 | Lippert et al. | |
| 2022/0039644 A1 | 2/2022 | Dayton et al. | |
| 2022/0047845 A1 | 2/2022 | Niederhauser et al. | |
| 2022/0105312 A1 | 4/2022 | Davis | |
| 2022/0105318 A1 | 4/2022 | Davis et al. | |
| 2022/0118225 A1 | 4/2022 | Snyder et al. | |
| 2022/0176075 A1 | 6/2022 | Mcdermott et al. | |
| 2022/0218358 A1 | 7/2022 | Dagan et al. | |
| 2022/0273474 A1 | 9/2022 | Koop et al. | |
| 2022/0280147 A1 | 9/2022 | Davis | |
| 2022/0296850 A1 | 9/2022 | Lippert | |
| 2022/0323166 A1 | 10/2022 | Tilson et al. | |
| 2022/0378459 A1 | 12/2022 | Lippert | |
| 2023/0010697 A1 | 1/2023 | Sharma et al. | |
| 2023/0069698 A1 | 3/2023 | Hallauer et al. | |
| 2023/0071512 A1 | 3/2023 | Maggio et al. | |
| 2023/0082226 A1 | 3/2023 | Lippert et al. | |
| 2023/0285720 A1 | 9/2023 | Isogai | |
| 2023/0405276 A1 | 12/2023 | Cabiri | |
| 2024/0108853 A1 | 4/2024 | Dulal et al. | |
| 2024/0123196 A1 | 4/2024 | Lippert et al. | |
| 2024/0198059 A1 | 6/2024 | Lippert et al. | |
| 2024/0299710 A1 | 9/2024 | Davis et al. | |

FOREIGN PATENT DOCUMENTS

| | | | |
|---|---|---|---|
| AU | 774559 | | 7/2004 |
| AU | 2008229892 | | 10/2008 |
| BR | 9709363 | | 1/2000 |
| BR | 9712829 | | 1/2000 |
| CA | 2266685 | | 5/2006 |
| CA | 2255781 | | 3/2007 |
| CA | 2395149 | | 12/2008 |
| CN | 1225282 | A | 8/1999 |
| CN | 1230914 | | 10/1999 |
| CN | 1324285 | | 11/2001 |
| CN | 1422673 | | 6/2003 |
| CN | 1518428 | | 8/2004 |
| CN | 1781684 | | 6/2006 |
| CN | 1897892 | A | 1/2007 |
| CN | 101001660 | | 7/2007 |
| CN | 101209365 | A | 7/2008 |
| CN | 101304778 | | 11/2008 |
| CN | 201239164 | Y | 5/2009 |
| CN | 101815553 | A | 8/2010 |
| CN | 102049085 | A | 5/2011 |
| CN | 102107041 | A | 6/2011 |
| CN | 102438691 | A | 5/2012 |
| CN | 102548603 | A | 7/2012 |
| CN | 102639303 | A | 8/2012 |
| CN | 102824681 | A | 12/2012 |
| CN | 102847225 | A | 1/2013 |
| CN | 103301553 | A | 9/2013 |
| CN | 103566457 | A | 2/2014 |
| CN | 103764012 | A | 4/2014 |
| CN | 103799980 | A | 5/2014 |
| CN | 103860265 | A | 6/2014 |
| CN | 104271035 | A | 1/2015 |
| CN | 104302345 | A | 1/2015 |
| CN | 104427950 | A | 3/2015 |
| CN | 104602616 | A | 5/2015 |
| CN | 104602718 | A | 5/2015 |
| CN | 104619247 | A | 5/2015 |
| CN | 104759022 | A | 7/2015 |
| CN | 104812420 | A | 7/2015 |
| CN | 105209102 | A | 12/2015 |
| CN | 105228536 | A | 1/2016 |
| CN | 105361918 | A | 3/2016 |
| CN | 105545375 | A | 5/2016 |
| CN | 105582611 | A | 5/2016 |
| CN | 105682725 | A | 6/2016 |
| CN | 105682729 | A | 6/2016 |
| CN | 105828690 | A | 8/2016 |
| CN | 105979880 | A | 9/2016 |
| CN | 107206216 | A | 9/2017 |
| CN | 109125889 | A | 1/2019 |
| CN | 109715245 | A | 5/2019 |
| CN | 109789296 | A | 5/2019 |
| DE | 60036882 | | 7/2008 |
| DE | 69738235 | | 7/2008 |
| EP | 0521595 | A2 | 1/1993 |
| EP | 0998323 | A1 | 5/2000 |
| EP | 934141 | | 11/2005 |
| EP | 921754 | | 10/2007 |
| EP | 1239901 | | 10/2007 |
| EP | 1844911 | A1 | 10/2007 |
| EP | 1940498 | | 7/2008 |
| EP | 2964305 | | 1/2016 |
| EP | 2414022 | B1 | 8/2017 |
| EP | 3866902 | A1 | 8/2021 |
| ES | 2293660 | | 3/2008 |
| GB | 2478988 | A | 9/2011 |
| JP | 59102509 | | 6/1984 |
| JP | 06-154335 | A | 6/1994 |
| JP | 07-008560 | | 1/1995 |
| JP | 08-215313 | A | 8/1996 |
| JP | 08-243168 | A | 9/1996 |
| JP | 08-243169 | A | 9/1996 |
| JP | 08-308934 | | 11/1996 |
| JP | 09-288239 | A | 11/1997 |
| JP | 11294497 | | 10/1999 |
| JP | 2000-503225 | A | 3/2000 |
| JP | 2000116787 | | 4/2000 |
| JP | 2000-126301 | A | 5/2000 |
| JP | 2000511094 | | 8/2000 |
| JP | 2000343313 | | 12/2000 |
| JP | 2001500808 | | 1/2001 |
| JP | 2002543896 | | 12/2002 |
| JP | 2003011117 | | 1/2003 |
| JP | 2004-025340 | A | 1/2004 |
| JP | 2004136121 | | 5/2004 |
| JP | 2004329552 | | 11/2004 |
| JP | 2004535233 | | 11/2004 |
| JP | 2005-514115 | A | 5/2005 |
| JP | 2005-534407 | A | 11/2005 |

(56) References Cited

FOREIGN PATENT DOCUMENTS

| | | | |
|---|---|---|---|
| JP | 2005533594 | | 11/2005 |
| JP | 2007-514458 | A | 6/2007 |
| JP | 2007313638 | | 12/2007 |
| JP | 2008-178656 | A | 8/2008 |
| JP | 2008536639 | | 9/2008 |
| JP | 2010-029736 | A | 2/2010 |
| JP | 2010-503484 | A | 2/2010 |
| JP | 2010-535583 | A | 11/2010 |
| JP | 2010535588 | | 11/2010 |
| JP | 2011-206175 | A | 10/2011 |
| JP | 4805208 | | 11/2011 |
| JP | 4845313 | | 12/2011 |
| JP | 2012-502743 | A | 2/2012 |
| JP | 2012-522607 | A | 9/2012 |
| JP | 2013-106854 | A | 6/2013 |
| JP | 2013-523282 | A | 6/2013 |
| JP | 2013-176560 | A | 9/2013 |
| JP | 2014-023727 | A | 2/2014 |
| JP | 2015-073861 | A | 4/2015 |
| JP | 2015-181723 | A | 10/2015 |
| JP | 2015-186427 | A | 10/2015 |
| JP | 2016-013269 | A | 1/2016 |
| JP | 2017-169253 | A | 9/2017 |
| KR | 20000015896 | | 3/2000 |
| KR | 20000036139 | | 6/2000 |
| NL | 2017570 | B1 | 4/2018 |
| RU | 91674 | U1 | 2/2010 |
| TW | 412468 | | 11/2000 |
| WO | 9419039 | | 1/1994 |
| WO | 1994006503 | | 3/1994 |
| WO | 95/24237 | A2 | 9/1995 |
| WO | 97/25914 | A1 | 7/1997 |
| WO | 98/55173 | A1 | 12/1998 |
| WO | 98/58697 | A1 | 12/1998 |
| WO | 99/04847 | A1 | 2/1999 |
| WO | 9953824 | | 10/1999 |
| WO | 2004011076 | | 2/2004 |
| WO | 2006/025931 | A1 | 3/2006 |
| WO | 2006/058234 | A2 | 6/2006 |
| WO | 2006113863 | | 10/2006 |
| WO | 2007050718 | | 5/2007 |
| WO | 2008/034010 | A2 | 3/2008 |
| WO | 2009/020691 | A2 | 2/2009 |
| WO | 2009/020836 | A1 | 2/2009 |
| WO | 2009020961 | | 2/2009 |
| WO | 2009020962 | | 2/2009 |
| WO | 2009/058705 | A2 | 5/2009 |
| WO | 2009/143160 | A1 | 11/2009 |
| WO | 2010077692 | | 7/2010 |
| WO | 2010115163 | | 10/2010 |
| WO | 2011/123689 | A1 | 10/2011 |
| WO | 2014/005095 | A1 | 1/2014 |
| WO | 2014/077881 | A1 | 5/2014 |
| WO | 2014066104 | | 5/2014 |
| WO | 2014138580 | | 9/2014 |
| WO | 2016047499 | | 3/2016 |
| WO | 2016117238 | | 7/2016 |
| WO | 2016136609 | | 9/2016 |
| WO | 2016152194 | | 9/2016 |
| WO | 2016158671 | | 10/2016 |
| WO | 2017/151292 | A1 | 9/2017 |
| WO | 2018/017349 | A1 | 1/2018 |
| WO | 2018/017351 | A1 | 1/2018 |
| WO | 2018/052815 | A1 | 3/2018 |
| WO | 2018218216 | | 11/2018 |
| WO | 2020/217171 | A1 | 10/2020 |
| WO | 2021/150920 | A1 | 7/2021 |
| WO | 2022/159139 | A1 | 7/2022 |

OTHER PUBLICATIONS

Non-Final Office Action received for U.S. Appl. No. 16/281,046, mailed on Oct. 29, 2020, 18 pages.

International Search Report and Written Opinion for Application PCT/US2017/050602 mailed on Nov. 7, 2017.

International Search Report and Written Opinion received for PCT Patent Application No. PCT/US2020/030589, mailed on Jul. 17, 2020, 7 pages.

International Search Report and Written Opinion, PCT App. No. PCT/US2020/013754, mailed on Jun. 9, 2020, 11 pages.

Non-Final Office Action received for U.S. Appl. No. 15/606,607, mailed on Jun. 10, 2020, 26 pages.

U.S. Appl. No. 16/212,425, filed Dec. 6, 2018, Christian.

U.S. Appl. No. 16/281,046, filed Feb. 20, 2019, Snyder.

U.S. Appl. No. 16/439,894, filed Jun. 13, 2019, Lippert.

Canadian Office Action for CA2757655 dated Jan. 2, 2018.

EP10759515.9 Supplementary European Search Report dated Sep. 25, 2012.

European Search Report for EP09836735 dated Nov. 7, 2012.

Supplementary Partial European Search Report for EP14760849 mailed Oct. 11, 2016.

European Search Report for EP15197042.3 dated Apr. 11, 2016.

European Search Report for application No. 17184064.8 mailed on Jan. 5, 2018.

International Search Report and Written Opinion for PCT/US2009/067217 dated Dec. 16, 2010.

International Search Report and Written Opinion for PCT/US2010/029867 dated Jun. 1, 2010.

International Search Report and Written Opinion for PCT/US2014/021742 dated Aug. 27, 2014.

International Search Report and Written Opinion for PCT/US2017/041299 mailed on Oct. 2, 2017.

International Search Report and Written Opinion for PCT/US2017/041301 mailed on Oct. 2, 2017.

International Search Report and Written Opinion for PCT/US2017/041305 mailed on Oct. 2, 2017.

International Search Report and Written Opinion for application PCT/US2017/050802 mailed on Nov. 7, 2017.

International Search Report and Written Opinion for PCT/US2017/068056 mailed on Feb. 26, 2018.

International Search Report and Written Opinion for PCT/US2018/034756 mailed on Aug. 14, 2018.

International Search Report and Written Opinion for PCT/US2019/019046 mailed on May 17, 2019.

International Search Report and Written Opinion for PCT/US2019/021031 mailed on Jun. 18, 2019.

International Search Report and Written Opinion for PCT/US2018/034723 mailed on Sep. 5, 2018.

U.S. Appl. No. 12/633,727, filed Oct. 16, 2012, Office Action.

U.S. Appl. No. 12/633,727, filed Feb. 28, 2013, Notice of Allowance.

U.S. Appl. No. 12/753,831, filed Feb. 1, 2012, Office Action.

U.S. Appl. No. 12/753,831, filed May 31, 2012, Final Office Action.

U.S. Appl. No. 12/753,831, filed Mar. 21, 2014, Office Action.

U.S. Appl. No. 12/753,831, Aug. 29, 2014, Final Office Action.

U.S. Appl. No. 12/753,831, filed Apr. 14, 2015, Notice of Allowance.

U.S. Appl. No. 12/753,836, filed Dec. 9, 2011, Office Action.

U.S. Appl. No. 12/753,836, filed May 1, 2012, Final Office Action.

U.S. Appl. No. 12/753,836, filed Jul. 31, 2014, Office Action.

U.S. Appl. No. 12/753,836, filed Jan. 9, 2015, Final Office Action.

U.S. Appl. No. 12/753,836, filed Jun. 26, 2015, Office Action.

U.S. Appl. No. 12/753,836, filed Feb. 17, 2016, Final Office Action.

U.S. Appl. No. 12/753,836, filed Dec. 23, 2016, Office Action.

U.S. Appl. No. 12/753,836, filed Jul. 14, 2017, Final Office Action.

U.S. Appl. No. 12/753,836, filed Nov. 24, 2017, Notice of Allowance.

U.S. Appl. No. 12/753,839, filed Feb. 7, 2012, Office Action.

U.S. Appl. No. 12/753,839, filed May 31, 2012, Final Office Action.

U.S. Appl. No. 12/753,839, filed May 5, 2014, Office Action.

U.S. Appl. No. 12/753,842, filed Aug. 1, 2012 , Office Action.

U.S. Appl. No. 12/753,842, filed Jan. 9, 2013, Final Office Action.

U.S. Appl. No. 12/753,842, filed Jan. 29, 2014, Office Action.

U.S. Appl. No. 12/753,842, filed Sep. 4, 2014, Final Office Action.

U.S. Appl. No. 12/753,842, filed Dec. 29, 2014, Notice of Allowance.

(56)            References Cited

OTHER PUBLICATIONS

U.S. Appl. No. 12/753,842, filed Mar. 5, 2015, Office Action.
U.S. Appl. No. 12/753,849, filed May 10, 2011, Office Action.
U.S. Appl. No. 12/753,849, filed Oct. 18, 2011, Office Action.
U.S. Appl. No. 12/753,849, filed Jun. 6, 2012, Final Office Action.
U.S. Appl. No. 12/753,849, filed Jan. 3, 2013, Office Action.
U.S. Appl. No. 12/753,849, filed Oct. 9, 2013, Final Office Action.
U.S. Appl. No. 12/753,849, filed May 27, 2014, Office Action.
U.S. Appl. No. 12/753,849, filed Nov. 5, 2014, Interview Summary.
U.S. Appl. No. 12/753,849, filed Feb. 2, 2015, Notice of Allowance.
U.S. Appl. No. 12/753,849, filed Apr. 30, 2015, Notice of Allowance.
U.S. Appl. No. 12/753,855, filed Sep. 15, 2011, Office Action.
U.S. Appl. No. 12/753,855, filed Apr. 18, 2012, Final Office Action.
U.S. Appl. No. 12/753,855, filed Feb. 28, 2014, Office Action.
U.S. Appl. No. 12/753,855, filed Jan. 13, 2015, Final Office Action.
U.S. Appl. No. 12/753,855, filed May 21, 2015, Office Action.
U.S. Appl. No. 12/753,855, filed May 5, 2016, Office Action.
U.S. Appl. No. 12/753,855, filed Nov. 30, 2016, Notice of Allowance.
U.S. Appl. No. 12/753,858, filed May 10, 2011, Office Action.
U.S. Appl. No. 12/753,858, filed Oct. 19, 2011, Final Office Action.
U.S. Appl. No. 12/753,858, filed Feb. 3, 2012, Office Action.
U.S. Appl. No. 12/753,858, filed Jul. 18, 2012, Final Office Action.
U.S. Appl. No. 12/753,858, filed Mar. 29, 2013, Office Action.
U.S. Appl. No. 12/753,858, filed Jan. 17, 2014, Final Office Action.
U.S. Appl. No. 12/753,858, filed Sep. 4, 2014, Office Action.
U.S. Appl. No. 12/753,858, filed Nov. 4, 2014, Interview Summary.
U.S. Appl. No. 12/753,858, filed May 28, 2015, Final Office Action.
U.S. Appl. No. 12/753,858, filed Dec. 30, 2015, Office Action.
U.S. Appl. No. 12/753,858, filed Oct. 24, 2016, Office Action.
U.S. Appl. No. 12/753,858, filed Mar. 27, 2017, Office Action.
U.S. Appl. No. 12/753,858, filed Oct. 20, 2017, Final Office Action.
U.S. Appl. No. 12/753,858, filed Mar. 13, 2018, Office Action.
U.S. Appl. No. 12/753,858, filed Nov. 14, 2018, Final Office Action.
U.S. Appl. No. 12/753,858, filed Mar. 14, 2019, Notice of Allowance.
U.S. Appl. No. 13/901,375, filed Dec. 10, 2015, Office Action.
U.S. Appl. No. 13/901,375, filed Aug. 1, 2016, Office Action.
U.S. Appl. No. 13/901,375, filed Dec. 27, 2016, Notice of Allowance.
U.S. Appl. No. 14/199,675, filed Nov. 3, 2016, Office Action.
U.S. Appl. No. 14/199,675, filed May 18, 2017, Final Office Action.
U.S. Appl. No. 14/199,675, filed Sep. 6, 2017, Notive of Allowance.
U.S. Appl. No. 15/465,399, filed Apr. 23, 2018, Office Action.
U.S. Appl. No. 15/465,399, filed Sep. 10, 2018, Notice of Allowance.
U.S. Appl. No. 15/611,328, filed Mar. 27, 2019, Office Action.
U.S. Appl. No. 15/611,344, filed Mar. 26, 2019, Office Action.
U.S. Appl. No. 15/606,607, filed May 14, 2019, Office Action.
U.S. Appl. No. 15/611,328, filed Sep. 24, 2019, Final Office Action.
U.S. Appl. No. 15/848,878, filed Oct. 29, 2019, Office Action.
U.S. Appl. No. 15/611,344, filed Nov. 12, 2019, Final OFfice Action.
U.S. Appl. No. 15/606,607, filed Nov. 19, 2019, Final Office Action.
U.S. Appl. No. 15/698,553, filed Nov. 27, 2019, Office Action.
U.S. Appl. No. 15/848,878, filed Feb. 5, 2020, Office Action.
U.S. Appl. No. 16/212,425, filed Mar. 16, 2020, Office Action.
U.S. Appl. No. 15/698,553, filed May 15, 2020, Notice of Allowance.
U.S. Appl. No. 15/611,344, filed May 21, 2020, Office Action.
Final Office Action received for U.S. Appl. No. 16/281,046, mailed on May 11, 2021, 18 pages.
International Search Report and Written Opinion received for PCT Patent Application No. PCT/US21/14656, mailed on Apr. 28, 2021, 8 pages.
Final Office Action received for U.S. Appl. No. 16/212,425, mailed on Aug. 3, 2020, 14 pages.
Final Office Action received for U.S. Appl. No. 15/848,878, mailed on Aug. 27, 2020, 13 pages.
Non-Final Office Action received for U.S. Appl. No. 15/611,328, mailed on Jun. 29, 2020, 13 pages.
Non-Final Office Action received for U.S. Appl. No. 15/917,255, mailed on Aug. 17, 2020, 12 pages.
Final Office Action received for U.S. Appl. No. 15/848,878, mailed on Sep. 22, 2021, 12 pages.
International Preliminary Report on Patentability received for PCT Patent Application No. PCT/US2020/013754, mailed on Jul. 29, 2021, 8 pages.
Non-Final Office Action received for U.S. Appl. No. 15/848,878, mailed on Jun. 3, 2021, 13 pages.
International Search Report and Written Opinion received for PCT Patent Application No. PCT/US21/042753, mailed on Nov. 5, 2021, 14 pages.
Non-Final Office Action received for U.S. Appl. No. 16/616,139, mailed on Oct. 26, 2021, 11 pages.
Final Office Action received for U.S. Appl. No. 17/216,127, mailed on Jun. 13, 2022, 8 pages.
Non-Final Office Action received for U.S. Appl. No. 16/616,220, mailed on Jun. 3, 2022, 20 pages.
Final Office Action received for U.S. Appl. No. 16/616,220, mailed on Oct. 12, 2022, 17 pages.
Non-Final Office Action received for U.S. Appl. No. 16/742,211, mailed on Aug. 15, 2022, 20 pages.
Non-Final Office Action received for U.S. Appl. No. 17/036,302, mailed on Mar. 1, 2023, 29 pages.
Penumbra Augments Vascular Franchise with Latest Indigo System Launch and Expands Medical/Scientific Leadership, Jul. 14, 2020, https://investors.penumbrainc.com/investors-relations/press-releases/press-release-details/2020/Penumbra-Augments-Vascular-Franchise-with-Latest-Indigo-System-Launch-and-Expands-MedicalScientific-Leadership/default.aspx.
Strength of Materials/Torsion, Wikibooks, 3 pp., accessed Feb. 22, 2023 (en.wikibooks.org/wiki/Strength_of_Materials/Torsion) (last edited Feb. 1, 2022) (Year: 2022).
U.S. Patent Application filed Feb. 20, 2019 by Snyder, U.S. Appl. No. 16/281,046, U.S. Appl. No. 16/281,046.
U.S. Patent Application Jun. 13, 2019, by Lippert, U.S. Appl. No. 16/439,894, U.S. Appl. No. 16/439,894.
Chinese Search Report for Chinese Application No. 201780070242.X, dated Sep. 14, 2016, 4 pages.
International Search Report and Written Opinion received for PCT Patent Application No. PCT/US2021/053647, mailed on Dec. 28, 2021, 9 pages.
International Search Report and Written Opinion received for PCT Patent Application No. PCT/US2021/053652, mailed on Dec. 28, 2021, 9 pages.
Non-Final Office Action received for U.S. Appl. No. 17/177,782, mailed on Nov. 4, 2022, 7 pages.
Final Office Action received for U.S. Appl. No. 16/742,211, mailed on Mar. 14, 2023, 22 pages.
Non-Final Office Action received for U.S. Appl. No. 17/177,782, mailed on Jan. 23, 2023, 14 pages.
Office Action received for European Patent Application No. 19710207.2, mailed on Dec. 4, 2023, 4 pages.
Supplementary European Search Report received for EP Patent Application No. 21744674.9, mailed on Feb. 7, 2024, 9 pages.
Non-Final Office Action received for U.S. Appl. No. 16/616,220, mailed on Nov. 5, 2024, 24 pages.
Non-Final Office Action received for U.S. Appl. No. 18/661,472, mailed on Dec. 6, 2024, 20 pages.
Requirement for Restriction/Election received for U.S. Appl. No. 18/589,282, mailed on Dec. 30, 2024, 5 pages.
Final Office Action received for U.S. Appl. No. 17/154,777, mailed on Apr. 17, 2024, 17 pages.
Final Office Action received for U.S. Appl. No. 17/836,863, mailed on Jun. 25, 2024, 6 pages.
Non-Final Office Action received for U.S. Appl. No. 17/382,271, mailed on May 14, 2024, 22 pages.
Non-Final Office Action received for U.S. Appl. No. 17/493,265, mailed on Jun. 11, 2024, 19 pages.
Final Office Action received for U.S. Appl. No. 17/036,302, mailed on Jul. 30, 2024, 17 pages.

(56)                References Cited

OTHER PUBLICATIONS

Final Office Action received for U.S. Appl. No. 17/382,271, mailed on Sep. 16, 2024, 9 pages.

Non-Final Office Action received for U.S. Appl. No. 17/752,600, mailed on Sep. 10, 2024, 11 pages.

Requirement for Restriction/Election received for U.S. Appl. No. 17/493,281, mailed on Oct. 9, 2024, 13 pages.

European Search Report received for EP Patent Application No. 21878402, mailed on Aug. 14, 2024, 13 pages.

Intention to grant received for European Patent Application No. 23188821.5, mailed on Aug. 14, 2024, 6 pages.

International Search Report and Written Opinion received for PCT Patent Application No. PCT/US2023/075485, mailed on Mar. 26, 2024, 19 pages.

International Search Report and Written Opinion received for PCT Patent Application No. PCT/US22/42514, mailed on Dec. 28, 2022, 11 pages.

International Search Report and Written Opinion received for PCT Patent Application No. PCT/US22/42517, mailed on Feb. 7, 2023, 11 pages.

Non-Final Office Action received for U.S. Appl. No. 18/589,282, mailed on Mar. 11, 2025, 11 pages.

Requirement for Restriction/Election received for U.S. Appl. No. 17/752,600, mailed on Apr. 25, 2024, 5 pages.

* cited by examiner

INTRAVASCULAR DEVICE WITH ENHANCED ONE-BEAM CUT PATTERN

CROSS-REFERENCE TO RELATED APPLICATIONS

This application claims priority to and the benefit of U.S. Provisional Patent Application Ser. No. 62/842,216, filed May 2, 2019 and titled "INTRAVASCULAR DEVICE WITH ENHANCED ONE-BEAM CUT PATTERN," the entirety of which is incorporated herein by this reference.

BACKGROUND

Interventional devices such as guidewires and catheters are frequently utilized in the medical field to perform delicate procedures deep within the human body. Typically, a catheter is inserted into a patient's femoral, radial, carotid, or jugular vessel and navigated through the patient's vasculature to the heart, brain, or other targeted anatomy as required. Often, a guidewire is first routed to the targeted anatomy, and one or more catheters are subsequently passed over the guidewire and routed to the targeted anatomy. Once in place, the catheter can be used to deliver drugs, stents, embolic devices, radiopaque dyes, or other devices or substances for treating the patient in a desired manner.

In many applications, such an interventional device must be angled through the tortuous bends and curves of a vasculature passageway to arrive at the targeted anatomy. For example, directing a guidewire and/or catheter to portions of the neurovasculature requires passage through the internal carotid artery and other tortuous paths. Such an interventional device requires sufficient flexibility, particularly closer to its distal end, to navigate such tortuous pathways.

In some cases, portions of the device are microfabricated to increase flexibility. For example, a guidewire may include an outer elongated tube that includes a series of machine-cut fenestrations near the distal end and sometimes at other locations. The cuts are typically arranged to define a series of axially extending "beams" that connect a series of circumferentially extending "rings."

While such microfabricating techniques are beneficial for increasing the flexibility of elongated intravascular components, several challenges remain. There is thus a long felt and ongoing need for improved intravascular devices and methods that enable the manufacture of such devices.

SUMMARY

Disclosed are intravascular devices, including guidewires and microcatheters, having enhanced one-beam cut patterns. An elongated member includes a plurality of fenestrations that define a plurality of axially extending beams interspersed between a plurality of circumferentially extending rings. The beams are formed using a dual-pass cutting method in which a blade makes two rotationally offset cutting passes at each longitudinal location of the elongated member. The resulting beam has enhanced structural features that avoid overly sharp edges and minimize structural weak points.

In one embodiment, an intravascular device includes an elongated member extending between a proximal end and a distal end along a longitudinal axis, the elongated member having a plurality of fenestrations that define a plurality of axially extending beams and circumferentially extending rings. At least one beam includes an interior surface, an exterior surface, and a pair of lateral surfaces, wherein an angle formed between the interior surface and one or both of the lateral surfaces is less than 135 degrees.

In one embodiment, a method of manufacturing an intravascular device comprises the steps of: providing a piece of stock material; passing a blade into the stock material to form a first cut in the stock material without passing completely through the stock material, the blade being oriented such that a cutting edge is substantially perpendicular to a longitudinal axis of the stock material; rotating the stock material relative to the blade without longitudinally advancing the stock material relative to the blade; and passing the blade into the stock material to form a second cut.

It is to be understood that both the foregoing general description and the following detailed description are exemplary and explanatory only and are intended to provide further explanation of the invention as claimed.

BRIEF DESCRIPTION OF THE DRAWINGS

Various objects, features, characteristics and advantages of the invention will become apparent and more readily appreciated from the following description of the embodiments, taken in conjunction with the accompanying drawings and the appended claims, all of which form a part of this specification wherein like reference numerals designate corresponding parts in the various figures and wherein the various elements depicted are not necessarily drawn to scale; and wherein:

DETAILED DESCRIPTION

Overview of Intravascular Devices

Figure 1:
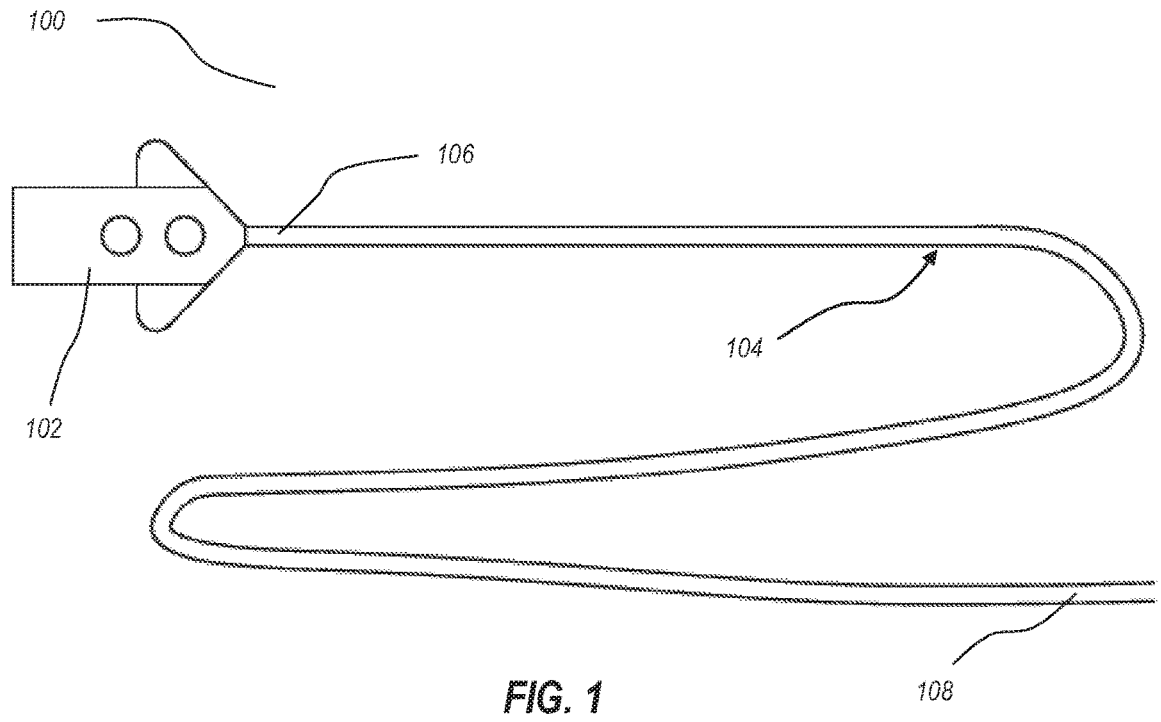
FIG. 1 illustrates an exemplary intravascular device such as a guidewire or microcatheter.

FIG. 1 illustrates an exemplary intravascular device 100 that comprises an elongated member 104 extending between a proximal end 106 and a distal end 108. An optional handle/hub/torquer 102 may be attached at the proximal end 106. The elongated member 104 may be, for example, a guidewire or a microcatheter.

The elongated member 104 may include a plurality of fenestrations cut into its outer surface. The fenestrations may be formed by cutting one or more pieces of stock material to form a cut pattern which leaves the fenestrations. The fenestrations can provide a variety of benefits, including increasing the flexibility of the elongated member 104. In some embodiments, the fenestrations are arranged to provide enhanced flexibility (relative to a similar section of stock material lacking fenestrations) while maintaining sufficient outer circumferential structure for effectively transmitting torque.

The elongated member 104 may be any length necessary for navigating a patient's anatomy to reach a targeted anatomical area. A typical length may be within a range of about 50 to 300 cm, for example. In a catheter embodiment, the outer diameter of the elongated member 104 may be within a range of about 0.010 inches to about 0.150 inches, though larger or smaller diameters may also be utilized according to preferences and/or application needs. In a guidewire embodiment, the outer diameter of the elongated member 104 may be about 0.014 inches, or may be within a range of about 0.008 to 0.145 inches, though larger or smaller sizes may also be utilized according to user preferences and/or application needs.

The elongated member 104, in a catheter embodiment, is typically formed from a material having an elastic modulus of about 3000 MPa to about 4500 MPa, or about 3500 MPa to about 4000 MPa. In one exemplary embodiment, the elongated member 104 is formed from or includes polyether ether ketone (PEEK). Other polymers with higher moduli may also be utilized where cost and/or fabrication considerations warrant it. In some embodiments, the elongated member 104 includes or is formed from a nickel-titanium alloy having superelastic properties at body temperature. In some embodiments, at least a portion of the elongated member 104 (e.g., a proximal portion) is formed from a stainless steel or other material with similar stress-strain and elastic modulus properties. Typically, if the elongated member 104 is formed from two or more different materials, the higher modulus material(s) are used at more proximal sections and the lower modulus material(s) are used at more distal sections.

Figure 2:
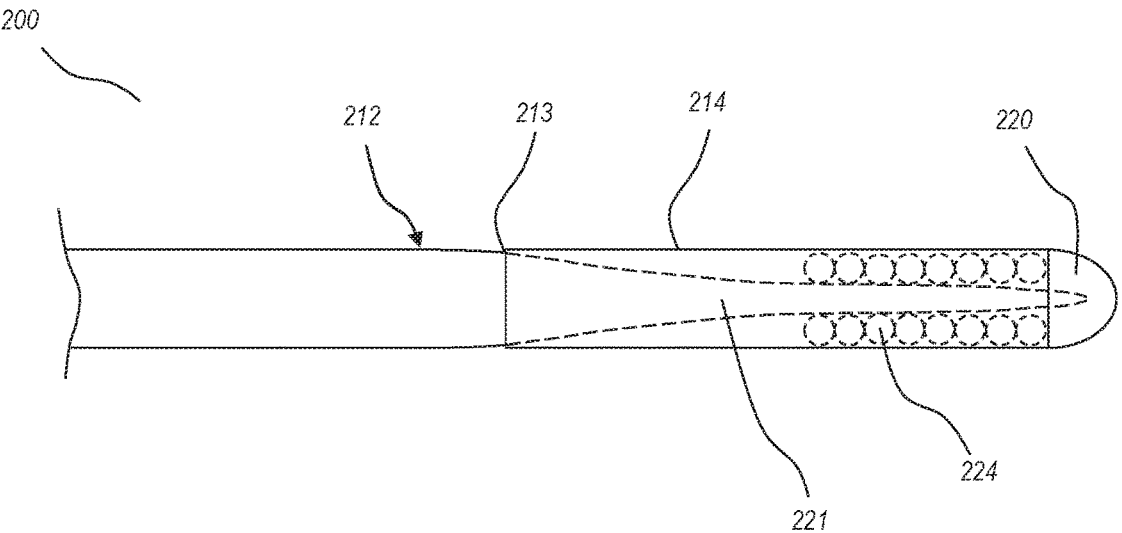
FIG. 2 illustrates the distal end of an embodiment of an intravascular device configured as a guidewire.

FIG. 2 illustrates the distal end of an embodiment of an intravascular device configured as a guidewire 200. The embodiment illustrated in FIG. 2 may represent the distal end 108 of a guidewire embodiment of the elongated member 104 of FIG. 1. The embodiment shown in FIG. 2 includes an inner member configured as a core 212. Other embodiments may additionally or alternatively include one or more other inner members, such as one or more inner tube structures.

The illustrated guidewire 200 includes a core 212 and a tube structure 214 coupled to the core 212. As shown, a distal section 221 of the core 212 extends into the tube 214 and is surrounded by the tube 214. In some embodiments, the distal section 221 of the core 212 is ground so as to progressively taper to a smaller diameter (e.g., about 0.002 inches) at the distal end. The distal section 221 of the core 212 may have a round cross-section, rectangular cross-section, or other suitable cross-sectional shape. In this example, the core 212 and the tube 214 have substantially similar outer diameters at the attachment point 213 where they adjoin and attach to one another.

The tube 214 may be coupled to the core 212 (e.g., using adhesive, soldering, and/or welding) in a manner that allows torsional forces to be transmitted from the core 212 to the tube 214 and thereby to be further transmitted distally by the tube 214. A medical grade adhesive 220 may be used to couple the tube 214 to the core 212 at the distal end of the device and to form an atraumatic covering.

The guidewire 200 may also include one or more coils such as coil 224 disposed within the tube 214 so as to be positioned between an outer surface of the distal section of the core 212 and an inner surface of the tube 214. The coil 224 may be formed from a radiopaque material, such as platinum. The illustrated coil 224 is formed as one integral piece. In alternative embodiments, the coil 224 includes a plurality of separate sections stacked, positioned adjacent to one another, and/or interlocked through intertwining.

The tube 214 may include micro-fabricated fenestrations configured to provide effective flexibility and torquability of the intravascular device. Some embodiments may additionally or alternatively include cuts formed in the core 212 itself, such as along the distal section 221 of the core.

Standard One-Beam Cut Patterns

Figure 3:
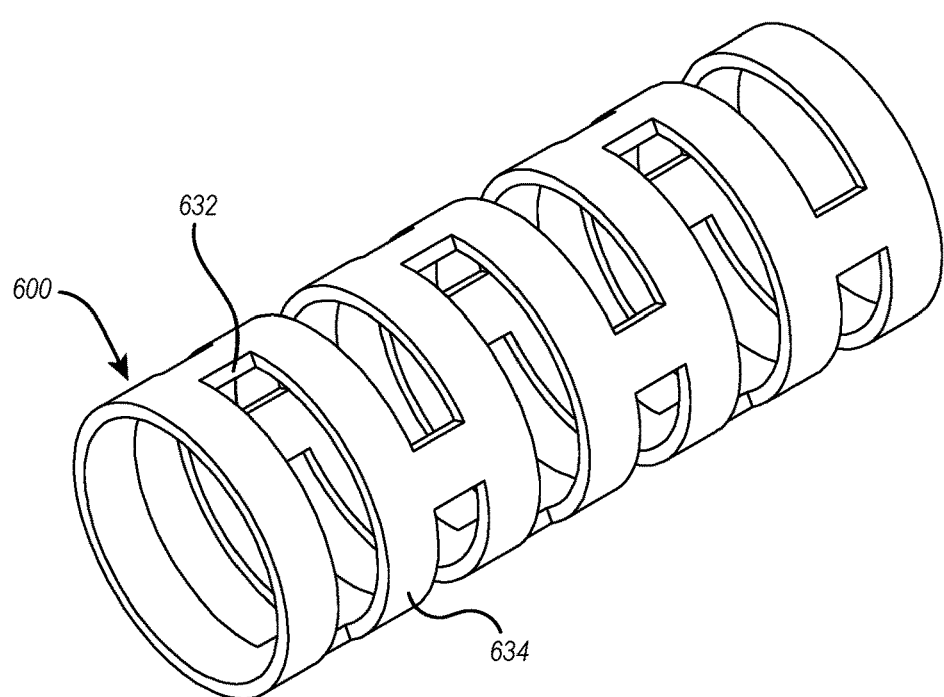
FIG. 3 illustrates an elongated member with a one-beam cut pattern.

FIG. 3 illustrates an elongated member 900 having a plurality of beams 932 and rings 934. The elongated member 900 is an example of a one-beam cut pattern because a single beam 932 is disposed between each pair of adjacent rings 934. In this example, each successive beam is rotationally offset by about 180 degrees from the preceding beam 932. Other embodiments may have different rotational offset patterns or may omit a rotational offset such that the beams are aligned on a single side of the elongated member 900.

Some embodiments may include beams 932 arranged in a "helical" pattern, or a non-linear pattern such as a "distributed" pattern, an "imperfect ramp" pattern, a "sawtooth" pattern, or a combination thereof each in a different section of the elongated member 900. These cut patterns are described in greater detail in PCT International Application Number PCT/US2018/034756, published as International Publication Number WO 2018/218216 A1, which is incorporated herein by this reference in its entirety.

In some embodiments, the rings and beams of an intravascular device may be encapsulated in a polymer. Intravascular devices, including guidewires and microcatheters, having polymer encapsulated microfabricated structures are described in greater detail in U.S. Pat. Nos. 9,067,332, 9,950,137, 9,067,333, and 9,072,873, which are each entirely incorporated herein by this reference.

Figure 4:
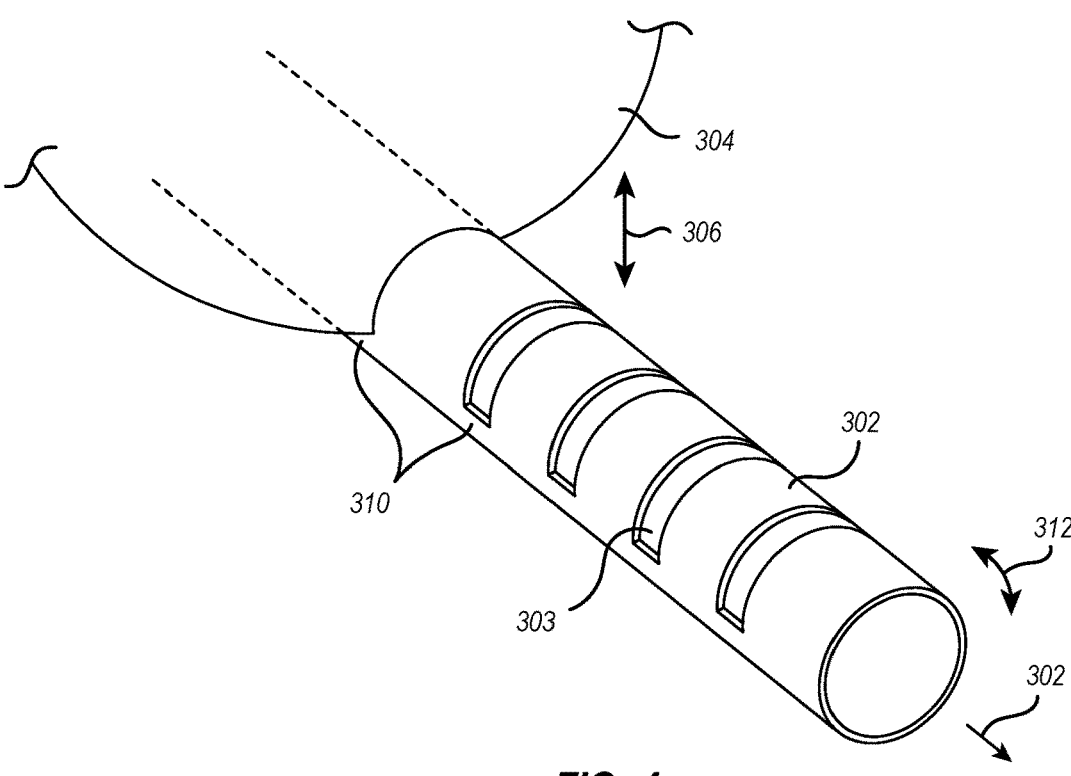
FIG. 4 illustrates a typical process for forming a one-beam cut pattern in a piece of stock material.

FIG. 4 illustrates a typical process for forming a one-beam cut pattern in a piece of stock material 302. The stock material 302 (typically a tube structure) is positioned in a cutting machine having a blade 304 (or a plurality of blades). As indicated by arrows 306, the blade 304 is moveable along an axis that is perpendicular to the longitudinal axis of the stock material 302 to form the fenestrations 303. Although the blade 304 is shown here as moving up and down along a vertical axis, other configurations may have a blade (or a plurality of blades) that move along a horizontal axis or even a diagonal axis.

To make a cut, the blade 304 is brought into contact with the stock material 302 and moved inward until the cut is made at the desired depth and a resulting beam 310 remains in the stock material 302. The blade 304 is then withdrawn from the stock material 302. The stock material 302 is then longitudinally moved relative to the blade 304, as indicated by arrow 308, until the next desired cut location is aligned with the blade 304. The process may then be repeated to form the desired number of cuts.

Cut depth and/or spacing between cuts may be varied from one device to the next, or even from one section of a device to another section of the same device. For example, sections intended to form distal portions of an intravascular device may include cuts that are relatively deeper and/or with relatively less spacing in order to increase the relative flexibility at the distal portion.

In some implementations, such as those that form helical or non-linear patterns, the stock material 302 may be rotated between successive cuts or between successive sets of cuts to allow for rotational offsets in the resulting beams, as indicated by arrows 312. Additional details related to cutting machines and related methods of manufacture are described in United States Issued U.S. Pat. No. 10,232,141, which is incorporated herein by this reference in its entirety.

Figure 5A:
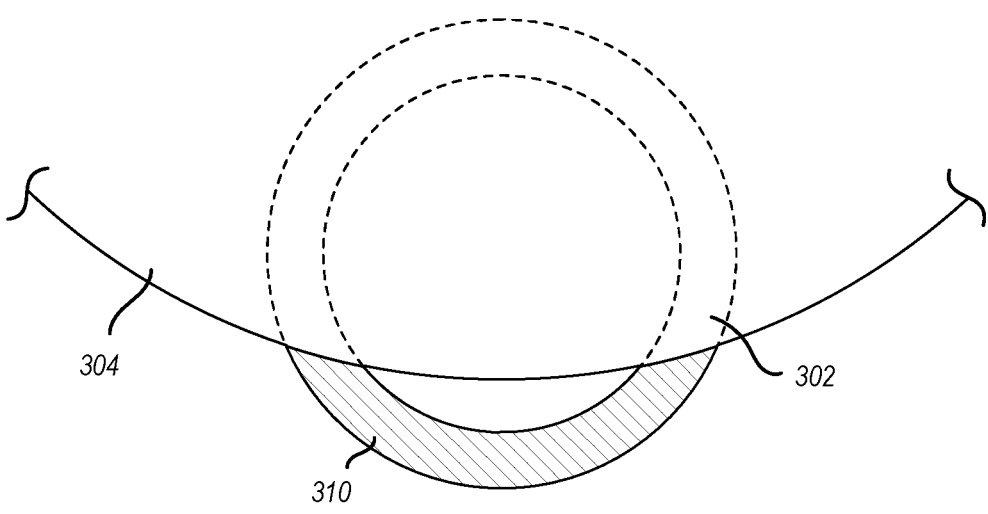
FIGS. 5A and 5B illustrate the structure of a beam that results from the standard cutting procedure shown in FIG. 4.
Figure 5B:
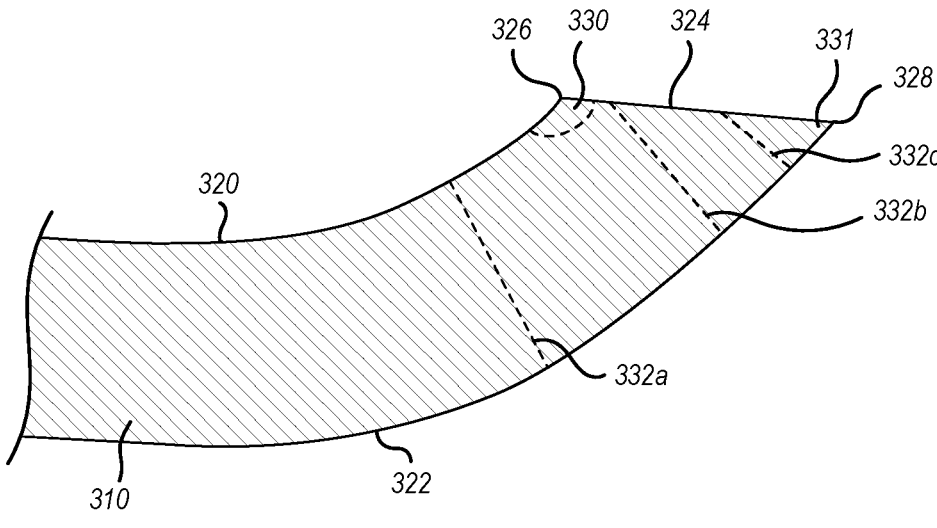

FIGS. 5A and 5B illustrate in greater detail the structure of the beam 310 that results from the standard cutting procedure shown in FIG. 4. FIG. 5A shows a front, cross-sectional view of the stock material 302 along a line that runs parallel to the blade path of a particular cut, and FIG. 5B shows an expanded view of an edge section of the resulting beam 310. As shown, the blade 304 typically has a diameter significantly larger than the diameter of the stock material 302 (typical blade diameters may range from 2 to 4 inches, for example). FIG. 5A shows the blade 304 at its deepest point within the stock material 302. After the blade 304 is withdrawn, the resulting beam 310 remains.

As best shown in FIG. 5B, the resulting beam 310 includes an interior surface 320, an exterior surface 322, and two lateral surfaces 324 (only one shown in FIG. 5B). Each lateral surface 324 joins the interior surface 320 along an interior edge 326, and joins the exterior surface 322 along an exterior edge 328. Angle 330 is formed where the interior surface 320 joins the lateral surface 324.

Because of the geometry of the cut, angle 330 is significantly greater than 90 degrees, and will typically be about 135 degrees. As a structural consequence of the size of angle 330, the radial thickness of the beam 310 thins out from the interior edge 326 to the exterior edge 328. The "radial thickness" refers to the thickness of the beam along a radial line extending from the geometric center of the cross section of the tube structure 302 to the exterior surface 322. Thus, while the beam 310 has substantially uniform radial thickness across much of its circumferential length (as indicated by radial line 332a), the radial thickness tapers between the interior edge 326 and the exterior edge 328 (as indicated by progressively shorter radial lines 332b and 332c).

Another structural consequence of that edge 328 will be relatively "sharp." That is, the angle 331 formed between lateral surface 324 and exterior surface 322 will be relatively small, such as about 45 degrees or less.

Enhanced One-Beam Cut Patterns

Figure 6A:
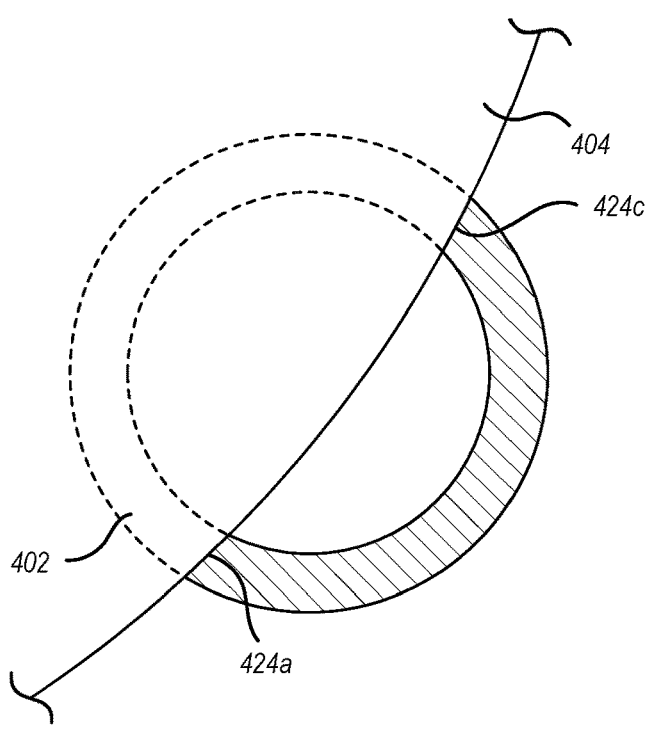
FIGS. 6A through 6C illustrate an alternative cutting procedure and the improved structure of a beam that results from the alternative cutting procedure.
Figure 6B:
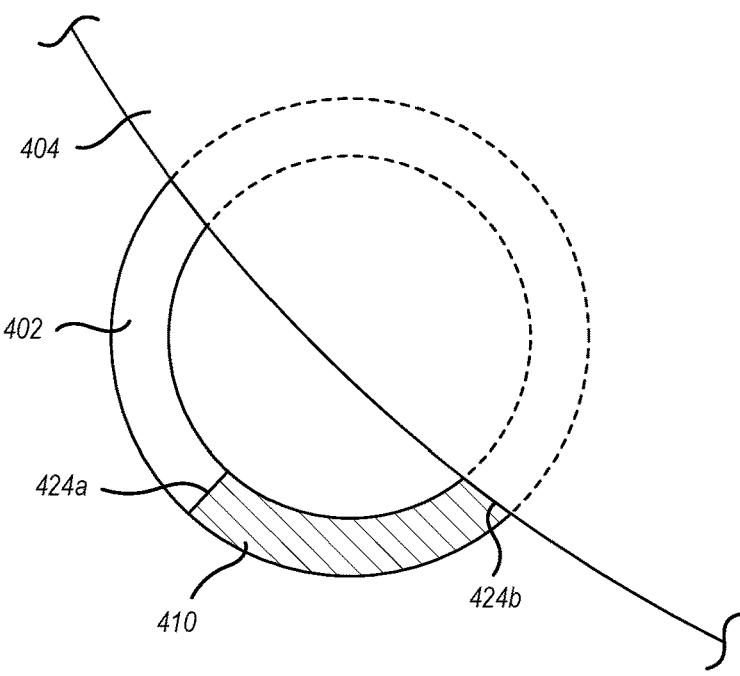
Figure 6C:
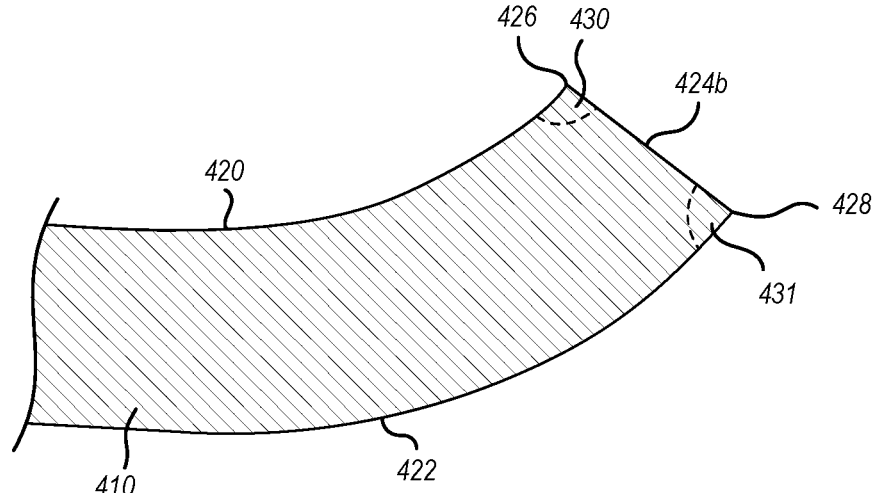

FIGS. 6A through 6C illustrate an alternative method for forming a beam 410 in a section of stock material 402. As shown in FIG. 6A, the blade 404 is first passed into the stock material 402 to a relatively shorter depth compared to the standard cut shown in FIG. 5A. For example, where the standard cut shown in FIG. 5A typically has a depth of about 70% of the stock material diameter or more, the initial cut depth shown in FIG. 6A is approximately 50% (e.g., about 30% to about 70%).

After the initial cut is formed, the stock material 402 is rotated relative to the blade 404 to allow the blade 404 to pass a second time into the stock material 402, as shown in FIG. 6B. The stock material 402 maintains the same longitudinal position relative to the blade during the first and second passes of the blade 404 so that the second cut is within the same plane as the first. During the first cut, a first lateral surface 424a is formed and a temporary lateral surface 424c is formed. The second cut then removes the temporary lateral surface 424c and cuts additional material to form the second lateral surface 424b.

Although the sequence from FIG. 6A and to FIG. 6B gives the appearance that the blade 404 is rotated clockwise relative to the stock material 402, it will be understood that this is for illustrative convenience only, and that any suitable means of relative rotation between the stock material 402 and blade 404 may be utilized by rotating the blade 404, the stock material 402, or both. Typically, the stock material 402 will be rotated relative to a rotationally static blade 404. The relative rotation is preferably about 90 degrees (e.g., about 60 degrees to about 120 degrees, or about 75 degrees to about 105 degrees).

FIG. 6C illustrates an expanded view of an edge section of resulting beam 410. The resulting beam 410 includes an interior surface 420, an exterior surface 422, and a pair of lateral surfaces 424 (with the single lateral surface 424b shown here). Each lateral surface 424 joins the interior surface 420 along an interior edge 426, and joins the exterior surface 422 along an exterior edge 428. Angle 430 is formed where the interior surface 420 joins the lateral surface 424.

As compared to angle 330 of the beam 310 shown in FIG. 5B, the angle 430 of beam 410 is markedly smaller. For example, the angle 430 may have a value within a range having a lower endpoint of about 75, 80, 85, or 90 degrees and an upper endpoint of about 130, 120, 110, or 100 degrees. Most preferably, the angle 430 is approximately 90 degrees such that lateral surface 424b is substantially perpendicular to interior surface 420.

The structure of the beam 410 provides a marked improvement over the standard beam 310. For example, the beam 410 avoids the "sharp" exterior edge 428 present in the standard beam 310. In other words, the angle 431 formed between the lateral surface 424 and the exterior surface 422 is greater than 45 degrees, such as about 50 degrees to about 90 degrees.

The improved beam 410 also avoids the tapering profile of the standard beam 310, and has more uniform radial thickness across the circumferential length of the beam 410. This beneficially minimizes structural weak points and provides greater fatigue life to the beam 410.

The dual-pass cutting process has also surprisingly been found to increase manufacturing efficiency and yields as compared to the standard, single-pass process. Even though the number of blade passes is doubled, the dual-pass process requires less depth per cut and typically forms more accurate cuts. This has been found to more than make up for the additional time required to do two cuts per beam.

ADDITIONAL EXEMPLARY EMBODIMENTS

The following is a selection of exemplary embodiments of the disclosed intravascular device and related methods. These are presented only by way of example and are not intended to limit the scope of the invention in any way.

Embodiment 1

An intravascular device comprising an elongated member extending between a proximal end and a distal end along a longitudinal axis, the elongated member having a plurality of fenestrations that define a plurality of axially extending beams and circumferentially extending rings. At least one beam includes an interior surface, an exterior surface, and a pair of lateral surfaces, wherein an angle formed between the interior surface and one or both of the lateral surfaces is less than 135 degrees.

Embodiment 2

The device of Embodiment 1, wherein the angle is between about 75 degrees and about 130 degrees.

Embodiment 3

The device of Embodiment 1 or 2, wherein the angle is between about 80 degrees and about 120 degrees, or between about 85 degrees and about 110 degrees, or between about 90 degrees and about 100 degrees, or wherein the angle is approximately 90 degrees.

Embodiment 4

The device of any one of Embodiments 1-3, wherein the elongated member is a tube structure.

Embodiment 5

The device of Embodiment 4, further comprising a core disposed within the tube structure.

Embodiment 6

The device of Embodiment 4 or Embodiment 5, further comprising an inner tube disposed within the tube structure.

Embodiment 7

The device of any one of Embodiments 4-6, further comprising one or more coils disposed within the tube structure, the one or more coils optionally comprising one or more radiopaque coils.

Embodiment 8

The device of any one of Embodiments 1-7, wherein the elongated member comprises a polymer.

Embodiment 9

The device of any one of Embodiments 1-8, wherein the rings and beams are encapsulated in a polymer.

Embodiment 10

The device of any one of Embodiments 1-9, wherein the elongated member comprises a nickel-titanium alloy.

Embodiment 11

The device of any one of Embodiments 1-10, wherein the elongated member comprises stainless steel.

Embodiment 12

The device of any one of Embodiments 1-11, wherein the elongated member is formed from two or more different materials.

Embodiment 13

The device of any one of Embodiments 1-12, wherein the at least one beam has a substantially uniform thickness across its circumferential length.

Embodiment 14

The device of any one of Embodiments 1-13, wherein an angle formed between the exterior surface and one or both lateral surfaces is greater than about 45 degrees.

Embodiment 15

The device of any one of Embodiments 1-14, wherein the intravascular device is a guidewire.

Embodiment 16

The device of any one of Embodiments 1-15, wherein the intravascular device is a microcatheter.

Embodiment 17

An intravascular device comprising an elongated member extending between a proximal end and a distal end along a longitudinal axis, the elongated member having a plurality of fenestrations that define a plurality of axially extending beams and circumferentially extending rings. At least one beam includes an interior surface, an exterior surface, and a pair of lateral surfaces, wherein an angle formed between the interior surface and one or both of the lateral surfaces is between about 75 degrees and about 130 degrees, and wherein an angle formed between the exterior surface and one or both lateral surfaces is greater than about 45 degrees.

Embodiment 18

A method of manufacturing an intravascular device such as in any one of Embodiments 1-17, the method comprising: providing a piece of stock material; passing a blade into the stock material to form a first cut in the stock material without passing completely through the stock material, the blade being oriented such that a cutting edge is substantially perpendicular to a longitudinal axis of the stock material; rotating the stock material relative to the blade without longitudinally advancing the stock material relative to the blade; and passing the blade into the stock material to form a second cut.

Embodiment 19

The method of Embodiment 18, wherein the stock material is rotated relative to the blade by about 60 degrees to about 120 degrees.

Embodiment 20

The method of Embodiment 18 or Embodiment 19, wherein the first cut is made by passing the blade into the stock material to a depth of about 30% to about 70% of the diameter of the stock material.

Embodiment 21

The method of any one of Embodiments 18-20, wherein the second cut is made by passing the blade into the stock material to a depth of about 30% to about 70% of the diameter of the stock material.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. An intravascular device formed from a stock material, the intravascular device comprising:
   an elongated member extending between a proximal end and a distal end along a longitudinal axis, and having a plurality of fenestrations that define a plurality of axially extending beams and circumferentially extending rings in a one-beam cut pattern, wherein between each pair of adjacent circumferentially extending rings is disposed a single axially extending beam without other axially extending beams;
   wherein at least one beam of the one-beam cut pattern includes an interior surface, an exterior surface, and a pair of lateral surfaces, wherein the lateral surfaces are substantially planar;
   wherein an angle formed between the interior surface and one or both of the lateral surfaces is between about 75 degrees and about 120 degrees;
   wherein an angle formed between the exterior surface and one or both lateral surfaces is greater than about 45 degrees; and
   wherein the at least one beam of the one-beam cut pattern has a shape resulting from cutting the stock material to a depth of 30% to 70% of the stock material diameter from a first angle, and cutting the stock material to a depth of 30% to 70% of the stock material diameter from a second angle, wherein the first angle and the second angle are 60 degrees to 120 degrees apart.

2. The device of claim 1, wherein the angle formed between the interior surface and one or both of the lateral surfaces is between about 80 degrees and about 120 degrees.

3. The device of claim 1, wherein the elongated member is a tube structure.

4. The device of claim 3, further comprising a core disposed within the tube structure.

5. The device of claim 3, further comprising an inner tube disposed within the tube structure.

6. The device of claim 3, further comprising one or more coils disposed within the tube structure.

7. The device of claim 1, wherein the elongated member comprises a polymer.

8. The device of claim 1, wherein the rings and beams are encapsulated in a polymer.

9. The device of claim 1, wherein the elongated member comprises a nickel-titanium alloy.

10. The device of claim 1, wherein the elongated member comprises stainless steel.

11. The device of claim 1, wherein the elongated member is formed from two or more different materials.

12. The device of claim 1, wherein the at least one beam has a substantially uniform thickness across its circumferential length.

13. The device of claim 1, wherein the angle formed between the exterior surface and one or both lateral surfaces is about 50 degrees to about 90 degrees.

14. The device of claim 1, wherein the intravascular device is a guidewire.

15. The device of claim 1, wherein the intravascular device is a microcatheter.

16. An intravascular device formed from a stock material, the intravascular device comprising:
   an elongated member extending between a proximal end and a distal end along a longitudinal axis, and having a plurality of fenestrations that define a plurality of axially extending beams and circumferentially extending rings in a one-beam cut pattern, wherein between each pair of adjacent circumferentially extending rings is disposed a single axially extending beam without other axially extending beams;
   wherein at least one beam of the one-beam cut pattern includes an interior surface, an exterior surface, and a pair of lateral surfaces;
   wherein an angle formed between the interior surface and one or both of the lateral surfaces is between about 75 degrees and about 130 degrees, and
   wherein an angle formed between the exterior surface and one or both lateral surfaces is greater than about 45 degrees, and
   wherein the at least one beam of the one-beam cut pattern has a shape resulting from cutting the stock material to a depth of 30% to 70% of the stock material diameter from a first angle, and cutting the stock material to a depth of 30% to 70% of the stock material diameter from a second angle, wherein the first angle and the second angle are 60 degrees to 120 degrees apart.

17. An intravascular device formed from a stock material, the intravascular device comprising:
   an elongated member extending between a proximal end and a distal end along a longitudinal axis, and having a plurality of fenestrations that define a plurality of axially extending beams and circumferentially extending rings in a one-beam cut pattern, wherein between each pair of adjacent circumferentially extending rings is disposed a single axially extending beam without other axially extending beams;
   a core disposed within the tube structure; and
   one or more coils disposed within the tube structure;
   wherein at least one beam of the one-beam cut pattern includes an interior surface, an exterior surface, and a pair of lateral surfaces, wherein the lateral surfaces are substantially planar;
   wherein an angle formed between the interior surface and one or both of the lateral surfaces is about 80 degrees to about 120 degrees;
   wherein an angle formed between the exterior surface and one or both lateral surfaces is about 50 degrees to about 90 degrees; and
   wherein the at least one beam of the one-beam cut pattern has a shape resulting from cutting the stock material to a depth of 30% to 70% of the stock material diameter from a first angle, and cutting the stock material to a depth of 30% to 70% of the stock material diameter from a second angle, wherein the first angle and the second angle are 60 degrees to 120 degrees apart.

18. The device of claim 1, wherein the lateral surfaces of the at least one beam are substantially perpendicular to interior surface.

\* \* \* \* \*